US012285274B2

(12) United States Patent
Yang et al.

(10) Patent No.: US 12,285,274 B2
(45) Date of Patent: Apr. 29, 2025

(54) SYSTEMS AND METHODS FOR GENERATING CALIBRATION IMAGES FOR COUCH POSITION CALIBRATION

(71) Applicant: SHANGHAI UNITED IMAGING HEALTHCARE CO., LTD., Shanghai (CN)

(72) Inventors: Hongcheng Yang, Shanghai (CN); Supratik Bose, Houston, TX (US); Xuan Wu, Shanghai (CN); Jonathan Maltz, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 281 days.

(21) Appl. No.: 17/806,256

(22) Filed: Jun. 9, 2022

(65) Prior Publication Data

US 2022/0313202 A1 Oct. 6, 2022

Related U.S. Application Data

(63) Continuation of application No. PCT/CN2020/118167, filed on Sep. 27, 2020.

(30) Foreign Application Priority Data

Dec. 11, 2019 (WO) ................ PCT/CN2019/124645

(51) Int. Cl.
*A61B 5/00* (2006.01)
*A61B 5/055* (2006.01)
(Continued)

(52) U.S. Cl.
CPC ............ *A61B 5/704* (2013.01); *A61B 5/0036* (2018.08); *A61B 5/055* (2013.01); *A61B 5/706* (2013.01);
(Continued)

(58) Field of Classification Search
CPC ..... A61B 2560/0223–0238; A61B 2005/1061; A61B 6/0492; A61B 5/706
See application file for complete search history.

(56) References Cited

U.S. PATENT DOCUMENTS

2004/0122311 A1* 6/2004 Cosman ................ A61B 90/14
600/427
2004/0133980 A1 7/2004 Coppens et al.
(Continued)

FOREIGN PATENT DOCUMENTS

CN 2902196 Y 5/2007
CN 201006193 Y 1/2008
(Continued)

OTHER PUBLICATIONS

CN-105078501-A (Year: 2015).*
(Continued)

*Primary Examiner* — Joel Lamprecht
*Assistant Examiner* — Nyrobi Celestine
(74) *Attorney, Agent, or Firm* — METIS IP LLC

(57) ABSTRACT

The present disclosure provides a system and method for couch position calibration. The method may include obtaining one or more first images of a couch at one or more first locations in a first device, each of the one or more first images corresponding to one of the one or more first locations, wherein the couch includes a mark, and the mark intersects a first reference plane of the first device at a plurality of first points of the mark; determining, in each of the one or more first images, a first position of a representation of each of the plurality of first points; obtaining correlation information between the first position and actual position of each of the plurality of first points; and determining one or more calibration images based on the correlation information and the one or more first images.

20 Claims, 12 Drawing Sheets

(51) Int. Cl.
*A61B 6/04* (2006.01)
*A61B 6/58* (2024.01)

(52) U.S. Cl.
CPC .......... *A61B 6/0407* (2013.01); *A61B 6/0492* (2013.01); *A61B 6/582* (2013.01)

(56) References Cited

U.S. PATENT DOCUMENTS

| | | |
|---|---|---|
| 2008/0031414 A1 | 2/2008 | Coppens |
| 2008/0123924 A1 | 5/2008 | Nabatame et al. |
| 2008/0250565 A1 | 10/2008 | Timmerman et al. |
| 2011/0160589 A1* | 6/2011 | Fu .......................... A61B 8/08 600/443 |
| 2012/0316425 A1 | 12/2012 | Raleigh et al. |
| 2013/0267830 A1 | 10/2013 | Ojha et al. |
| 2014/0155736 A1 | 6/2014 | Vaidya et al. |
| 2016/0067525 A1 | 3/2016 | Bouchet et al. |
| 2017/0049529 A1 | 2/2017 | Hannemann et al. |
| 2017/0065233 A1 | 3/2017 | Yang |
| 2018/0025466 A1 | 1/2018 | Mazurkewitz et al. |
| 2018/0197303 A1 | 7/2018 | Jordan et al. |
| 2018/0280223 A1 | 10/2018 | Hiratsuka et al. |
| 2019/0029632 A1 | 1/2019 | Yang et al. |
| 2019/0030366 A1 | 1/2019 | Maltz |
| 2019/0175122 A1 | 6/2019 | Stahl et al. |
| 2019/0175942 A1 | 6/2019 | Stahl et al. |
| 2019/0201717 A1 | 7/2019 | Shangguan et al. |
| 2019/0239844 A1 | 8/2019 | Bose et al. |
| 2021/0346720 A1 | 11/2021 | Zhao et al. |

FOREIGN PATENT DOCUMENTS

| | | | |
|---|---|---|---|
| CN | 103054607 A | | 4/2013 |
| CN | 105078501 A | * | 11/2015 |
| CN | 108937987 A | | 12/2018 |
| CN | 109663223 A | | 4/2019 |
| CN | 110038233 A | | 7/2019 |
| DE | 102006036575 A1 | | 2/2008 |
| GB | 2561373 A | * | 10/2018 .............. A61B 6/04 |
| JP | H1076020 A | | 3/1998 |
| JP | H11290293 A | | 10/1999 |
| JP | 2002126106 A | | 5/2002 |

OTHER PUBLICATIONS

International Search Report in PCT/CN2020/118167 mailed on Dec. 30, 2020, 4 pages.
Written Opinion in PCT/CN2020/118167 mailed on Dec. 30, 2020, 4 pages.
International Search Report in PCT/CN2019/124645 mailed on Aug. 31, 2020, 4 pages.
Written Opinion in PCT/CN2019/124645 mailed on Aug. 31, 2020, 4 pages.
The Extended European Search Report in European Application No. 19955565.7 mailed on Nov. 7, 2022, 9 pages.

* cited by examiner

700

---

Obtaining one or more first images of a couch at one or more first locations in a first device, each of the one or more first images corresponding to one of the one or more first locations, wherein the couch includes a mark, and the mark intersects a first reference plane of the first device at a plurality of first points of the mark  — 710

Determining, in each of the one or more first images, a first position of a representation of each of the plurality of first points — 720

Obtaining correlation information between the first position and an actual position of each of the plurality of first points — 730

Determining one or more calibration images based on the correlation information and the one or more first images — 740

- 810: Obtaining a test first image of the couch at a test location in the first device, the test first image including a representation of a plurality of test first points of the mark

- 820: Determining, in the test first image, a test first position of a representation of each of the plurality of test first points

- 830: Obtaining a third image of the couch at the test location

- 840: Determining, based on the test first image and the third image, correlation information between the test first positions of the plurality of test first points and actual positions of the plurality of test first points in the couch

| Determining a reference calibration image corresponding to a second image from one or more calibration images based on a plurality of second points in the second image, the reference calibration image being obtained at a reference first location in a first device | 1110 |

↓

| Designating a coordinate of the reference first location along a longitudinal direction of the couch as a first coordinate of the second location along the longitudinal direction of the couch | 1120 |

↓

| Determining, in the reference calibration image, a reference calibration isocenter position of a representation of a first isocenter of the first device and a reference calibration position of each of the plurality of reference calibration points | 1130 |

↓

| Determining, based on the second isocenter, the second positions, the reference calibration positions, and the reference calibration isocenter position, a difference between a location of the couch in the first device and a location of the couch in the second device along the lateral direction of the couch | 1140 |

FIG. 11

SYSTEMS AND METHODS FOR GENERATING CALIBRATION IMAGES FOR COUCH POSITION CALIBRATION

CROSS-REFERENCE TO RELATED APPLICATIONS

This application is a continuation of International Application No. PCT/CN2020/118167, filed on Sep. 27, 2020, which claims the priority of International Application No. PCT/CN2019/124645, filed on Dec. 11, 2019, the contents of each of which are hereby incorporated by reference.

TECHNICAL FIELD

The present disclosure generally relates to systems and methods for imaged guided radiation therapy (IGRT), and more particularly, to methods and systems for generating calibration images for couch position calibration.

BACKGROUND

An image guided radiation therapy (IGRT) system employing an imaging device, such as a computed tomography (CT) device, concurrently with a treatment device, is widely used in clinical treatment for cancers and other conditions. During a radiation treatment using such an IGRT system, a subject (e.g., a patient) may lie on a couch and be moved with the couch between the imaging device and the treatment device. For example, the subject may be scanned or imaged under the imaging device, and receive a treatment under the treatment device. However, since the couch may deviate from its planned position when moving between the imaging device and the treatment device, the couch position in the imaging device and/or in the treatment device needs to be calibrated. Generally, the couch position calibration is based on calibration images. Thus, it is desirable to develop systems and methods for generating calibration images for couch position calibration.

SUMMARY

According to a first aspect of the present disclosure, a method for couch position calibration is provided. The method may be implemented on a machine including at least one processor and at least one storage device. The method may include obtaining one or more first images of a couch at one or more first locations in a first device, each of the one or more first images corresponding to one of the one or more first locations, wherein the couch includes a mark, and the mark intersects a first reference plane of the first device at a plurality of first points of the mark; determining, in each of the one or more first images, a first position of a representation of each of the plurality of first points; obtaining correlation information between the first position and an actual position of each of the plurality of first points; and determining one or more calibration images based on the correlation information and the one or more first images.

In some embodiments, the one or more first locations may include locations arranged at regular intervals along a longitudinal direction of the couch.

In some embodiments, the mark may include at least one of an N-shaped mark, an M-shaped mark, an S-shaped mark, a V-shaped mark, an A-shaped mark, or a W-shaped mark.

In some embodiments, the obtaining correlation information between the first position and actual position of each of the plurality of first points may include obtaining a test first image of the couch at a test location in the first device, the test first image including a representation of a plurality of test first points of the mark; determining, in the test first image, a test first position of a representation of each of the plurality of test first points; obtaining a third image of the couch at the test location; and determining, based on the test first image and the third image, the correlation information between the test first positions of the plurality of test first points and actual positions of the plurality of test first points in the couch.

In some embodiments, at least one of the first image, the calibration image, or the test first image is a 2D image, and the third image is a 3D image.

In some embodiments, the method may further include obtaining a second image of the couch at a second location in a second device, wherein the mark intersects a second reference plane of the second device at a plurality of second points of the mark; determining, in the second image, a second isocenter position of a representation of a second isocenter of the second device and a second position of a representation of each of the plurality of second points; and determining, based on the one or more calibration images, the second isocenter position, and the second positions, a difference between a location of the couch in the first device and a location of the couch in the second device.

In some embodiments, the difference between the location of the couch in the first device and the location of the couch in the second device may include a difference of a first coordinate of the second location along the longitudinal direction of the couch. The determining, based on the one or more calibration images, the second isocenter position, and the second positions, a difference between a location of the couch in the first device and a location of the couch in the second device may include determining, from the one or more calibration images and based on the plurality of second points in the second image, a reference calibration image corresponding to the second image, the reference calibration image being determined based on a reference first image, the reference first image being obtained at a reference first location in the first device; and designating a coordinate of the reference first location along a longitudinal direction of the couch as the first coordinate of the second location along the longitudinal direction of the couch.

In some embodiments, the determining, from the one or more calibration images and based on the plurality of second points in the second image, a reference calibration image may include determining a calibration feature among a plurality of calibration points of each of the one or more calibration images, each of the plurality of calibration points corresponding to one of the plurality of first points; determining a second feature among the plurality of second points of the second image; and determining, based on the calibration feature and the second feature, the reference calibration image.

In some embodiments, the determining, based on the calibration feature and the second feature, the reference calibration image may include identifying, from the one or more calibration images, a calibration image having the calibration feature that matches the second feature; and designating the identified calibration image as the reference calibration image.

In some embodiments, the plurality of second points may include a point A, a point B, and a point C. The second feature may include at least one of a first distance between the point A and the point B, a second distance between the point B and the point C, a ratio of the first distance to the second distance, a ratio of the second distance to the first distance, or a difference between the first distance and the second distance.

In some embodiments, the difference between the location of the couch in the first device and the location of the couch in the second device may include a difference between the location of the couch in the first device and the location of the couch in the second device along the lateral direction of the couch. The determining, based on the one or more calibration images, the second isocenter position, and the second positions, a difference between a location of the couch in the first device and a location of the couch in the second device further may include determining, in the reference calibration image, a reference calibration isocenter position of a representation of a first isocenter of the first device, and a reference calibration position of each of a plurality of reference calibration points; and determining, based on the second isocenter, the second positions, the reference calibration positions, and the reference calibration isocenter position, a difference between a location of the couch in the first device and a location of the couch in the second device along the lateral direction of the couch.

In some embodiments, the first device may include an imaging device, and the second device includes a treatment device. In some embodiments, the first device may include a treatment device, and the second device includes an imaging device.

According to a second aspect of the present disclosure, a system is provided. The system may include at least one storage device storing executable instructions, and at least one processor in communication with the at least one storage device. When executing the executable instructions, the at least one processor may cause the system to perform a method. The method may include obtaining one or more first images of a couch at one or more first locations in a first device, each of the one or more first images corresponding to one of the one or more first locations, wherein the couch includes a mark, and the mark intersects a first reference plane of the first device at a plurality of first points of the mark; determining, in each of the one or more first images, a first position of a representation of each of the plurality of first points; obtaining correlation information between the first position and an actual position of each of the plurality of first points; and determining one or more calibration images based on the correlation information and the one or more first images.

According to a third aspect of the present disclosure, a non-transitory computer-readable medium storing at least one set of instructions is provided. When executed by at least one processor, the at least one set of instructions may direct the at least one processor to perform a method. The method may include obtaining one or more first images of a couch at one or more first locations in a first device, each of the one or more first images corresponding to one of the one or more first locations, wherein the couch includes a mark, and the mark intersects a first reference plane of the first device at a plurality of first points of the mark; determining, in each of the one or more first images, a first position of a representation of each of the plurality of first points; obtaining correlation information between the first position and an actual position of each of the plurality of first points; and determining one or more calibration images based on the correlation information and the one or more first images.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 7 is a flowchart illustrating an exemplary process for determining calibration images according to some embodiments of the present disclosure;

FIG. 8 is a flowchart illustrating an exemplary process for determining correlation information between a first position of each of a plurality of first points of a mark in a first image and an actual position of each of a plurality of first points of a mark according to some embodiments of the present disclosure;

FIG. 11 is a flowchart illustrating an exemplary process for determining a difference between a location of the couch in the first device and a location of the couch in the second device according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Figure 2:
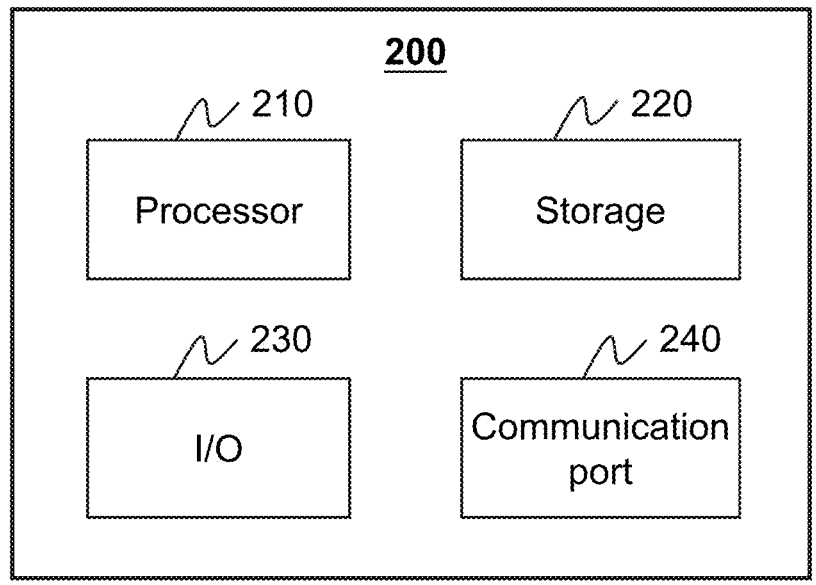
FIG. 2 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging and/or treatment, such as for disease diagnosis, treatment or research purposes. In some embodiments, the systems may include an RT system, a computed tomography (CT) system, an emission computed tomography (ECT) system, an X-ray photography system, a positron emission tomography (PET) system, or the like, or any combination thereof. For illustration purposes, the disclosure describes systems and methods for radiotherapy.

An aspect of the present disclosure relates to a couch position calibration system. The couch position calibration system may include a treatment device, an imaging device, and a couch being movable between the treatment device and the imaging device along a first direction in a first coordinate system. The couch may have a plurality of cross sections perpendicular to the first direction. The couch may also include a mark that extends along the first direction.

In some embodiments, when a subject is undergoing an image guided radiation therapy (IGRT), for example, a CT scanning and a radiotherapy, the subject may receive radiotherapy in an RT device after being scanned in a CT device. Specifically, the subject may lie on a couch for the CT scanning. After the CT scanning, the subject may be moved with the couch to a certain location in the RT device for radiotherapy. However, due to the deformation caused by, e.g., the moving of the couch and the accumulation of control errors, an offset between a positioning coordinate system of the CT device and a positioning coordinate system of the RT device may be generated, thereby affecting the efficiency of clinical operations and/or the efficacy of the radiotherapy. Some embodiments of the present disclosure relate to a calibration method and system for determining a difference between a location of the couch in the imaging device and a location of the couch in the treatment device by using a mark included in the couch.

Figure 1:
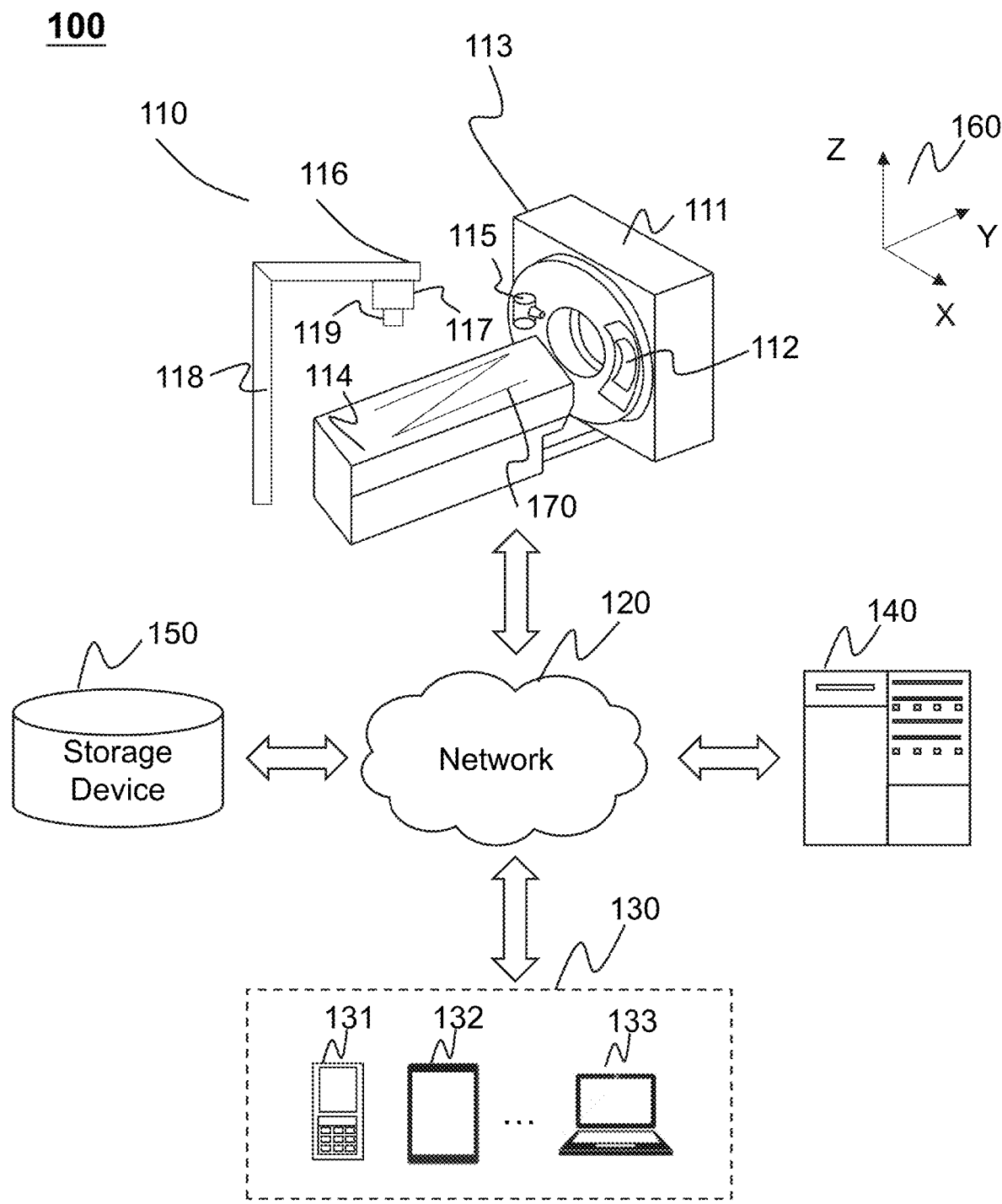
FIG. 1 is a schematic diagram illustrating an exemplary medical system including a couch position calibration system according to some embodiments of the present disclosure.

FIG. 1 is a schematic diagram illustrating an exemplary couch position calibration system according to some embodiments of the present disclosure. A couch position calibration system 100 may include a radiation delivery device 110, a network 120, a terminal 130, a processing device 140, and a storage device 150. In some embodiments, two or more components of the couch position calibration system 100 may be connected to and/or communicate with each other via a wireless connection (e.g., the network 120), a wired connection, or a combination thereof. The connection between the components of the couch position calibration system 100 may be variable. Merely by way of example, the radiation delivery device 110 may be connected to the processing device 140 through the network 120 or directly. As a further example, the storage device 150 may be connected to the processing device 140 through the network 120 or directly.

The radiation delivery device 110 may include an imaging device 113, a treatment device 116, a couch 114, or the like. The imaging device 113 may be configured to acquire an image of a subject prior to a radiotherapy treatment, during the radiotherapy treatment, and/or after the radiotherapy treatment. The subject may include a biological subject (e.g., a human being, an animal, a plant, or a portion thereof) and/or a non-biological subject (e.g., a phantom). For example, the imaging device may include a computed tomography (CT) device (e.g., a cone beam computed tomography (CBCT) device, a fan-beam computed tomography (FBCT) device), an ultrasound imaging device, a fluoroscopy imaging device, a magnetic resonance imaging (MRI) device, a single photon emission computed tomography (SPECT) device, a positron emission tomography (PET) device, an X-ray imaging device, or the like, or any combination thereof. For illustration purposes, the present disclosure takes a CT device as an exemplary imaging device 113. This is not intended to be limiting.

In some embodiments, the imaging device 113 may include an imaging radiation source 115, a detector 112, a gantry 111, or the like. The imaging radiation source 115 and the detector 112 may be mounted on the gantry 111. The imaging radiation source 115 may emit radioactive rays to the subject. The detector 112 may detect radiation events (e.g., x-ray photons, gamma-ray photons) emitted from the imaging region of the imaging device 113. In some embodiments, the detector 112 may include one or more detector units. The detector unit(s) may include a scintillation detector (e.g., a cesium iodide detector, a gadolinium oxysulfide detector), a gas detector, etc. The detector unit(s) may include a single-row detector and/or a multi-rows detector.

The treatment device 116 may be configured to deliver a radiotherapy treatment to the subject. The treatment device 116 may include a treatment radiation source 117, a gantry 118, and a collimator 119. The treatment radiation source 117 may be configured to emit treatment radiations towards the subject. In some embodiments, the treatment radiation source 117 may include a linear accelerator (LINAC). The collimator 119 may be configured to control the shape of the treatment radiations generated by the treatment radiation source 117.

In some embodiments, the couch 114 may be movable between the treatment device 116 and the imaging device 113 along a certain direction (e.g., a Y-axis direction of a coordinate system 160 as shown in FIG. 1). The couch 114 may include a mark 170 that extends along the certain direction. The mark 170 with the positioning feature may be used to determine a moving path of the couch 114. More descriptions regarding the couch 114 and/or mark 170 may be found elsewhere in the present disclosure. See, e.g., FIGS. 4A to 9 and relevant descriptions thereof.

The network 120 may include any suitable network that can facilitate the exchange of information and/or data for the couch position calibration system 100. In some embodiments, one or more components of the couch position calibration system 100 (e.g., the radiation delivery device 110, the terminal 130, the processing device 140, the storage device 150, etc.) may communicate information and/or data with one or more other components of the couch position calibration system 100 via the network 120. For example, the processing device 140 may obtain image data from the radiation delivery device 110 via the network 120. As another example, the processing device 140 may obtain user instructions from the terminal 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the couch position calibration system 100 may be connected to the network 120 to exchange data and/or information.

Figure 3:
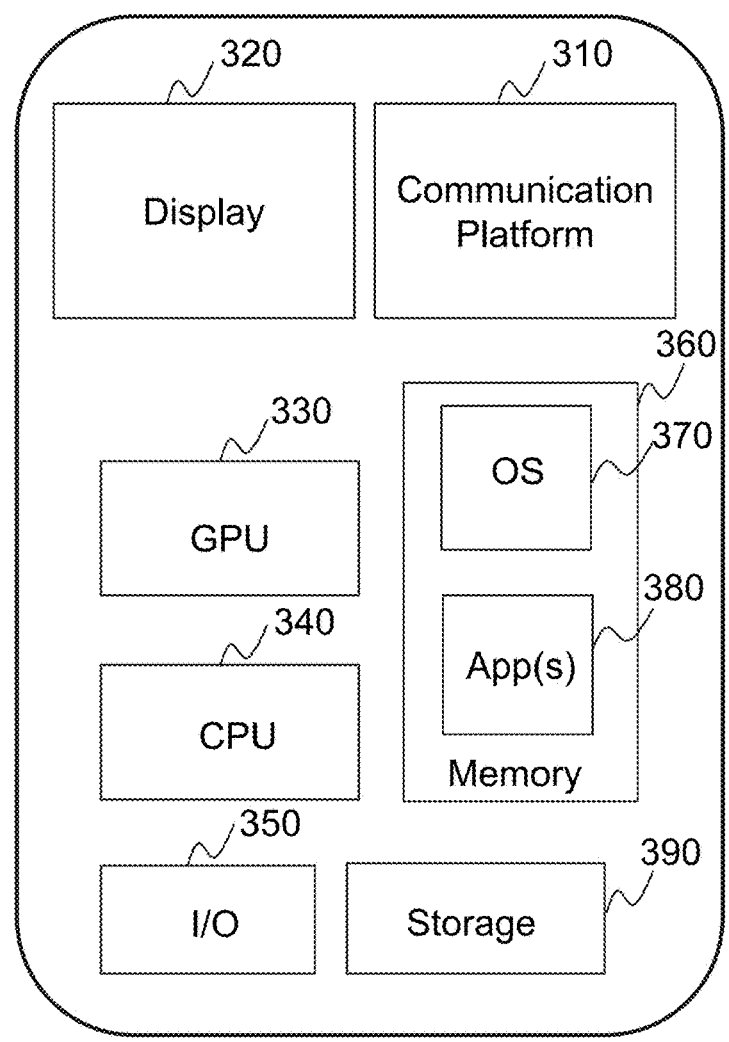
FIG. 3 is a schematic diagram illustrating hardware and/or software components of an exemplary mobile device according to some embodiments of the present disclosure.

The terminal 130 may enable user interaction between a user and the couch position calibration system 100. In some embodiments, the terminal 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. Merely by way of example, the terminal 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal 130 may be part of the processing device 140.

The processing device 140 may process information obtained from the radiation delivery device 110, the terminal 130, and/or the storage device 150. In some embodiments, the processing device 140 may be a single server or a server group. The server group may be centralized or distributed. In some embodiments, the processing device 140 may be local or remote. For example, the processing device 140 may access information stored in the radiation delivery device 110, the terminal 130, and/or the storage device 150 via the network 120. As another example, the processing device 140 may be directly connected to the radiation delivery device 110, the terminal 130 and/or the storage device 150 to access stored information. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components of the couch position calibration system 100 (e.g., the processing device 140, the terminal 130). One or more components of the couch position calibration system 100 may access the data and/or instructions stored in the storage device 150 via the network 120. In some embodiments, the storage device 150 may be directly connected to or communicate with one or more other components of the couch position calibration system 100 (e.g., the processing device 140, the terminal 130). In some embodiments, the storage device 150 may be part of the processing device 140.

For illustration purposes, a coordinate system 160 including an X-axis, a Y-axis, and a Z-axis is provided in FIG. 1. The X-axis and the Y-axis shown in FIG. 1 may be horizontal, and the Z-axis may be vertical. As illustrated, the positive X direction along the X-axis may be from the left side to the right side of the couch 114 viewed from the direction facing the front of the radiation delivery device 110; the positive Y direction along the Y-axis shown in FIG. 1 may be from the end to the head of the couch 114; the positive Z direction along the Z-axis shown in FIG. 1 may be from the lower part to the upper part of the gantry 118. In some embodiments, the direction along the X-axis may be referred to as the lateral direction of the couch. In some embodiments, the direction along the Y-axis may be referred to as the longitudinal direction of the couch. The origin of the coordinate system 160 may be located at any suitable position. For example, the origin may be located at the isocenter of the LINAC of the treatment device 116, and the coordinate system 160 may be referred to as an RT coordinate system. As another example, the imaging device 113 may be a CT device. The origin of the coordinate system 160 may be located at the rotation center of the gantry 111 of the CT device, and the coordinate system 160 may be referred to as a CT coordinate system. For the convenience of descriptions, coordinates of an entity along an X-axis, a Y-axis, and a Z-axis in a coordinate system are also referred to as an X-coordinate, a Y-coordinate, and Z-coordinate of the entity in the coordinate system, respectively.

It should be noted that the above description regarding the couch position calibration system 100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the couch position calibration system 100 may include one or more additional components and/or one or more components of the couch position calibration system 100 described above may be omitted. Additionally or alternatively, two or more components of the couch position calibration system 100 may be integrated into a single component. A component of the couch position calibration system 100 may be implemented on two or more sub-components. In some embodiments, the coordinate system 160 in FIG. 1 is an exemplary coordinate system for illustration purposes and may be modified. For example, the axes of the coordinate system 160 may be different from the axes exemplified above (e.g., the X-axis, the Y-axis, and the Z-axis). In addition, although the following descriptions discusses through various examples to determine a position of an entity by determining a coordinate of an entity in a certain coordinate system, it should be understood that the position of the entity may be determined by determining a coordinate in another coordinate system (e.g., a coordinate system that has a known transformation relationship with the certain coordinate system).

FIG. 2 is a schematic diagram illustrating exemplary hardware and/or software components of a computing device according to some embodiments of the present disclosure. The computing device 200 may be used to implement any component of the couch position calibration system 100 as described herein. For example, the processing device 140 and/or the terminal 130 may be implemented on the computing device 200, respectively, via its hardware, software program, firmware, or a combination thereof. Although only one such computing device is shown, for convenience, the computer functions relating to the couch position calibration system 100 as described herein may be implemented in a distributed fashion on a number of similar platforms, to distribute the processing load. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein.

The computer instructions may include, for example, routines, programs, objects, components, data structures, procedures, modules, and functions, which perform particular functions described herein. For example, the processor 210 may process image data obtained from the radiation delivery device 110, the terminal 130, the storage device 150, and/or any other component of the couch position calibration system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

The storage 220 may store data obtained from one or more components of the couch position calibration system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure. For example, the storage 220 may store a program for the processing device 140 to execute to check errors in replanning.

The I/O 230 may input and/or output signals, data, information, etc. In some embodiments, the I/O 230 may enable a user interaction with the processing device 140. In some embodiments, the I/O 230 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 140) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 120) to facilitate data communications. The communication port 240 may establish connections between the processing device 140 and the radiation delivery device 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device according to some embodiments of the present disclosure. In some embodiments, a terminal 130 and/or a processing device 140 may be implemented on a mobile device 300, respectively. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to the couch position calibration system 100. User interactions with the information stream may be achieved via the I/O 350 and provided to the processing device 140 and/or other components of the couch position calibration system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4A:
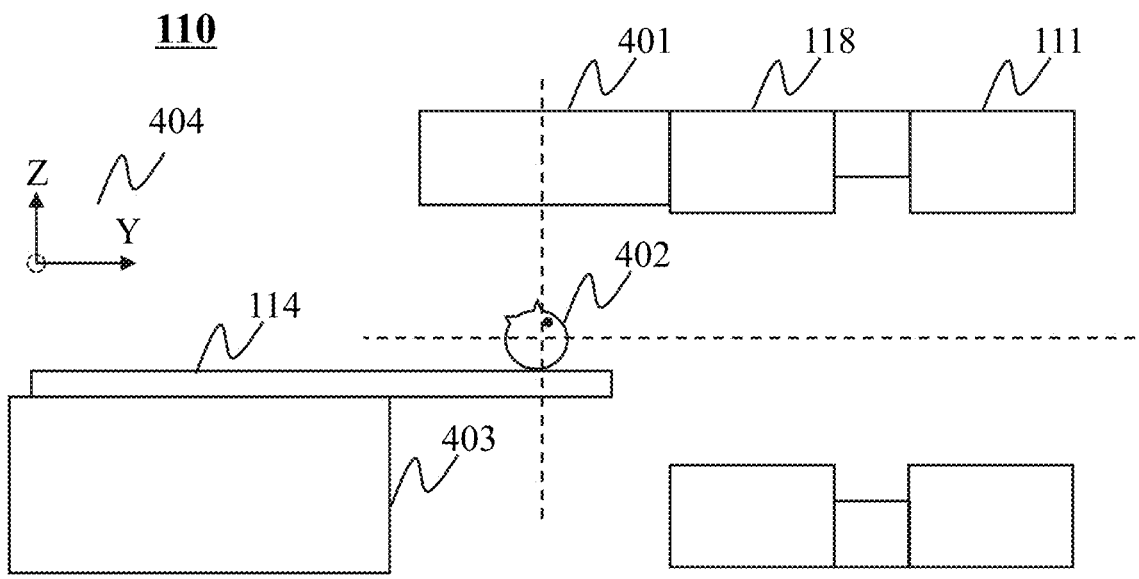
FIG. 4A is a schematic diagram illustrating an exemplary radiation delivery device according to some embodiments of the present disclosure.
Figure 4B:
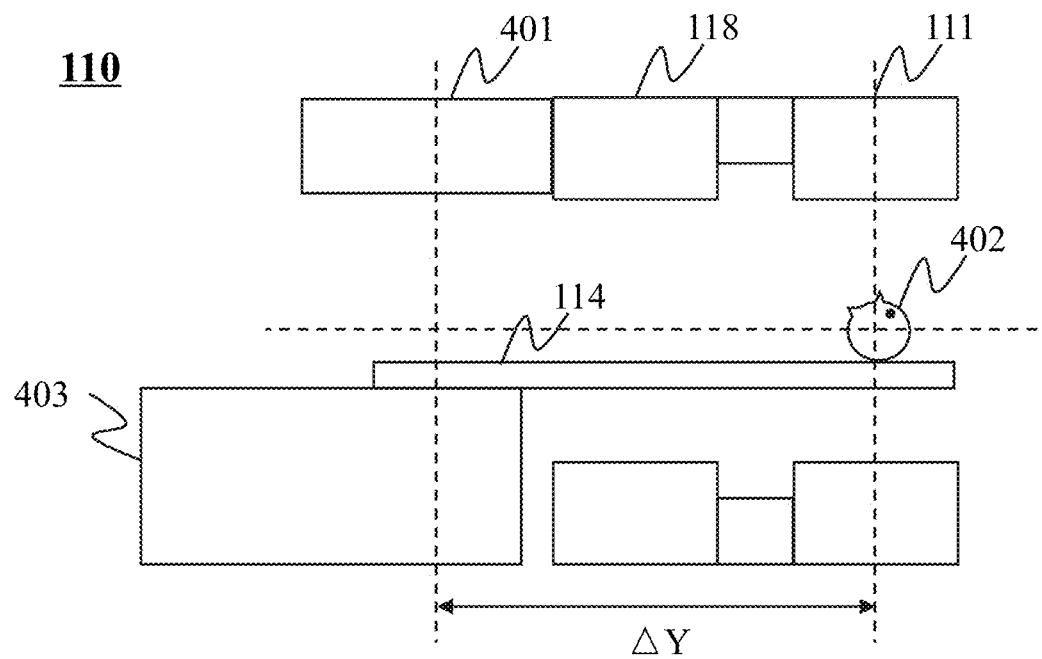
FIG. 4B is a schematic diagram illustrating an exemplary radiation delivery device according to some embodiments of the present disclosure.

FIGS. 4A and 4B are schematic diagrams illustrating an exemplary radiation delivery device 110 according to some embodiments of the present disclosure. The radiation delivery device 110 may include a treatment device, an imaging device (e.g., a CT device), a couch 114, and a couch base 403. The treatment device may include a treatment head 401 and a gantry 118. In some embodiments, the treatment head may include a LINAC, a treatment radiation source, a collimator, or the like, or any combination thereof. The imaging device may include a gantry 111, an X-ray source, a detector, or the like, or any combination thereof. The couch base 403 may be configured to support the couch 114.

In some embodiments, a subject may be placed on the couch 114 for treatment and/or imaging. The subject may include a biological subject and/or a non-biological subject. Exemplary biological subjects may include a human being, an animal, a plant, or a portion thereof (e.g., a cell, a tissue, an organ, etc.). In some embodiments, the subject may include a region of interest (ROI) 402. The ROI 402 may include a region of the subject including at least part of malignant tissue (e.g., a tumor, a cancer-ridden organ, or a non-cancerous target of radiation therapy) and/or other tissue (e.g., tissue surrounding the malignant tissue). For example, the ROI 402 may include a target and/or one or more organs-at-risk (OAR). A target may refer to a certain anatomical structure that needs to be tracked and/or monitored during a radiotherapy treatment. For example, the target may be a tumor, an organ with a tumor, tissue with a tumor, or any combination thereof, that needs to be treated by radiations. An OAR may include an organ (or a portion thereof) and/or tissue that are close to the target and not indented to be subjected to radiation but under the risk of radiation damage due to its proximity to the target.

In some embodiments, the couch 114 may be movable between the treatment device and the imaging device of the radiation delivery device 110 along a Y-axis direction in a coordinate system 404 as illustrated in FIG. 4A, so as to move the subject to different positions.

The coordinate system 404 may be a similar coordinate system as the reference coordinate system 160 as described in connection with FIG. 1. The coordinate system 404 may include the Y-axis, a Z-axis, and an X-axis (which is perpendicular to the plane formed by the Y-axis and the Z-axis). In some embodiments, the origin of the coordinate system 404 may be located at any suitable position. For example, the origin of the coordinate system 404 may be coincident with a mid-point of the head of the couch 114 (e.g., the leftmost edge or side of the couch as illustrated in FIG. 4A) when the subject is positioned as shown in FIG. 4A. In some embodiments, the position may be represented as by a set of coordinates (e.g., the X coordinate, the Y coordinate, and the Z coordinate) in the coordinate system 404. In some embodiments, the coordinate system 404 may also be referred to as a fixed coordinate system with respect to the radiation delivery device 110. A set of coordinates of an entity (e.g., the X coordinate, the Y coordinate, and the Z coordinate of the entity) in the coordinate system 404 may represent a position of the entity relative to the radiation delivery device 110.

In some embodiments, the radiation delivery device 110 may be used to deliver a radiotherapy treatment to the subject. Conventionally, before the subject begins to receive the radiotherapy treatment (e.g., days or weeks before the treatment commences), a planning image (e.g., a CT image) of the subject may be acquired using an imaging device, e.g., the imaging device of the radiation delivery device 110. As used herein, a planning image may refer to an image according to which a treatment plan for the subject is made. The treatment plan may describe how the radiotherapy treatment is planned to be performed on the subject, more specifically, how one or more beams are delivered to the ROI 402 of the subject during each treatment fraction over the course of treatment lasting a certain period of time, e.g., days. For example, the treatment plan may provide a total dose (e.g., 0.1 Gy, 10 Gy, 50 Gy, 100 Gy, etc.) and a dose distribution in the ROI 402.

Normally, to deliver the current fraction, the subject may be positioned at a position as illustrated in FIG. 4A, and be moved to a planned position as illustrated in FIG. 4B by moving the couch 114. For example, the couch 114 may move, according to an instruction, along a planned moving path to reach the planned position, wherein the planned moving path may be parallel with the Y-axis direction and extend for a specific distance $\Delta Y$ along the Y-axis direction as illustrated in FIG. 4B. However, due to one or more factors including, e.g., an operation error, the couch 114 may move along a moving path different from the planned moving path and reach a position that is different from the planned position. For example, the actual moving path of the couch 114 may have an angle with the Y-axis direction, which may result in a deviation between the actual location of the couch 114 and the planned position along the X-axis direction, and in turn a deviation between the actual location of the ROI 402 and the planned position of the ROI 402 along the X-axis direction. Merely by way of example, the angle between the actual moving path of the couch 114 and the Y-axis direction may be denoted as A (e.g., 0.1 degrees), and a distance of the actual moving path along the Y-axis direction may be denoted as D (e.g., 2100 mm). The deviation (denoted as $D_x$) between the actual location of the ROI 402 and the planned position of the ROI 402 along the X-axis direction may be determined according to a function $D_x = D \times \tan(A \times \pi/180)$. As another example, the actual moving distance of the couch 114 along the Y-axis direction may be smaller than or greater than the specific distance $\Delta Y$, which may result in a deviation between the actual location of the ROI 402 and the planned position of the ROI 402 along the Y-axis direction. As yet another example, due to deformation and/or displacement of the couch 114, the actual location of the ROI 402 may have a deviation with respect to the planned position of the ROI 402 along the Z-axis direction.

In some embodiments, a treatment image of the subject may be acquired in the treatment device, e.g., before the delivery of the radiotherapy. The treatment image and the planning image may need to be registered according to a common coordinate system so as to identify the anatomical change of the ROI 402. In some embodiments, the couch 114 may include a mark (e.g., a mark 170) having a positioning feature. More descriptions regarding the mark may be found elsewhere in the present disclosure. See, e.g., FIGS. 5A to 8 and relevant descriptions thereof.

Figure 5A:
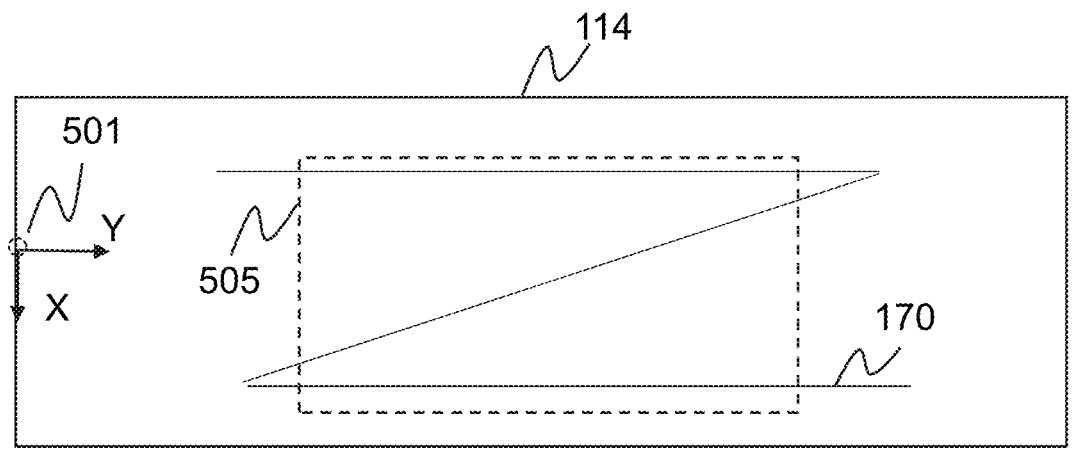
FIG. 5A is a schematic diagram of an exemplary couch according to some embodiments of the present disclosure.
Figure 5B:
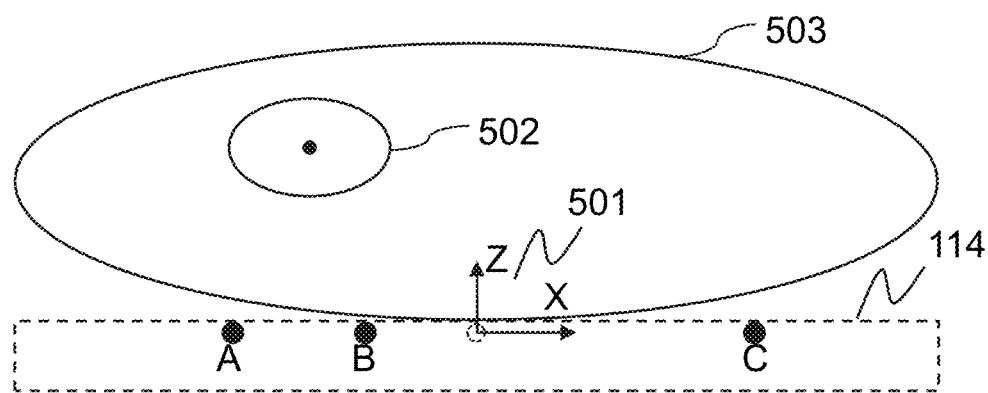
FIG. 5B is a schematic diagram of an exemplary couch according to some embodiments of the present disclosure.
Figure 5C:
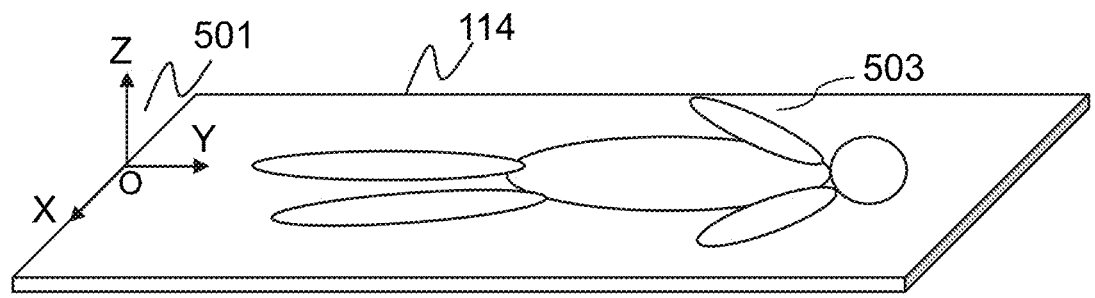
FIG. 5C is a schematic diagram of an exemplary couch according to some embodiments of the present disclosure.

FIGS. 5A to 5C are schematic diagrams of an exemplary couch 114 according to some embodiments of the present disclosure. FIG. 5A illustrates a top view of the couch 114. FIGS. 5B and 5C illustrate a section view and a perspective view of the couch 114 with a patient 503 lying on the couch 114, respectively. The couch 114 may be a component of a radiation delivery device (e.g., the radiation delivery device 110) that includes an imaging device and a treatment device. The radiation delivery device may be configured to treat and/or image the patient 503.

In treatment and/or imaging, the patient 503 may lie on the couch 114 along the Y-axis direction as shown in FIG. 5C. The couch 114 may be configured to move between the imaging device and the treatment device along the Y-axis direction to position the patient 503 to a certain position (e.g., a position for treatment or a position for imaging). The origin of the coordinate system 501 is located at any position, for example, a mid-point of the head of the couch 114 (e.g., the leftmost edge or side of the couch 114 in FIG. 5A). Optionally, the origin of the coordinate system 501 may move with the movement of the couch 114. In some embodiments, the coordinate system 501 may also be referred to as a coordinate system with respect to the couch 114. A set of coordinates (e.g., the X coordinate, the Y coordinate, and the Z coordinate) of an entity in the coordinate system 501 may represent a position of the entity relative to the couch 114.

As shown in FIG. 5A, the couch 114 may include a mark 170 extending along the Y-axis direction. In some embodiments, the mark 170 may be mounted on a surface of the couch 114 on which the patient 503 lies as illustrated in FIG. 5A via any mounting mechanism, such as glue, adhesive, or the like. Alternatively, the mark 170 may be mounted within the couch 114. In some embodiments, the density of the mark 170 may be different from the density of the couch 114, so that the mark 170 may be distinguished from the couch 114 in an image including the mark 170 (or a portion thereof) and the couch 114 (or a portion thereof). In some embodiments, the material of the mark 170 may be associated with the type of the imaging device of the radiation delivery device. For example, if the imaging device is a CT device, the mark 170 may include metal such as copper, iron, aluminum, or the like, or any combination thereof. As another example, if the imaging device is an MRI device, the mark 170 may include oil.

The mark 170 may have any suitable shape and/or size. In some embodiments, different portions of the mark 170 may have a uniform diameter. Optionally, the diameter of the mark 170 may be within a predetermined range, so that it may be able to be identified by the imaging device. For example, the diameter of the mark 170 may range from 0.2 millimeters (mm) to 1 mm, 0.5 mm to 1 mm, 1 mm to 2 mm, 3 mm to 5 mm, or the like. In some embodiments, the diameter of the mark 170 may be equal to 0.5 mm, 1 mm, 2 mm, 3 mm, 4 mm, or the like. In some embodiments, the mark 170 may cover a field of view (FOV) of the imaging device (e.g., an FOV as indicated by a dotted box 505 in FIG. 5A). As used herein, to "cover an FOV" may refer to that a length of the mark 170 along the Y-axis direction in the coordinate system 501 is equal to or greater than a length of the FOV along the Y-axis direction. For example, if the length of the FOV along the Y-axis direction is 900 mm, the length of the mark 170 along the Y-axis direction may be equal to any value greater than 900 mm, for example, 1000 mm, 1100 mm, 1200 mm, 1500 mm, etc.

In some embodiments, the mark 170 may have a particular shape so that a feature value of the mark corresponding to a location of the couch 114 can be determined when the couch 114 is located at a certain location in the imaging device 113 or the treatment device 116. In some embodiments, the feature values of the mark corresponding to different locations of the couch 114 may be different. In some embodiments, the mark 170 may have a plurality of intersection points with the reference plane of the imaging device 113 or the treatment device 116. For example, the mark 170 may include an N-shaped mark, an M-shaped mark, a W-shaped mark, or the like. In some alternative embodiments, the mark 170 may also have any other shape. For example, the mark 170 may include a V-shaped mark, an A-shaped mark, an S-shaped mark, etc. For illustration purposes, an N-shaped mark may be used as an example of the mark 170. As shown in FIG. 5B, for the mark 170 with an N-shape, a cross section (e.g., the reference plane of the imaging device 113) of the couch 114 includes points A, B, and C of the mark 170. The point B is located between the points A and C. As another example, the mark 170 may be a symbol or shape other than a letter. For instance, the mark 170 may be a non-letter shape that is asymmetric along the Y direction as illustrated in FIG. 5A, and has a plurality of intersection points with the reference plane of the imaging device 113 or the treatment device 116.

It should be noted that examples illustrated in FIGS. 4A to 4B and FIGS. 5A to 5C and the descriptions thereof are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. The shape, size, and/or position of a component in FIGS. 4A to 5C are illustrative and may be modified. Additionally or alternatively, the coordinate systems 404 and 501 exemplified above are provided for illustration purposes and not intended to be limiting. Merely by way of example, the origin of the coordinate system 501 may be located at a point other than the mid-point of the head of the couch 114, such as a mid-point of the end of the couch 114 that is opposite the head of the couch 114 along the Y-axis direction, as illustrated in FIG. 5C.

Figure 6:
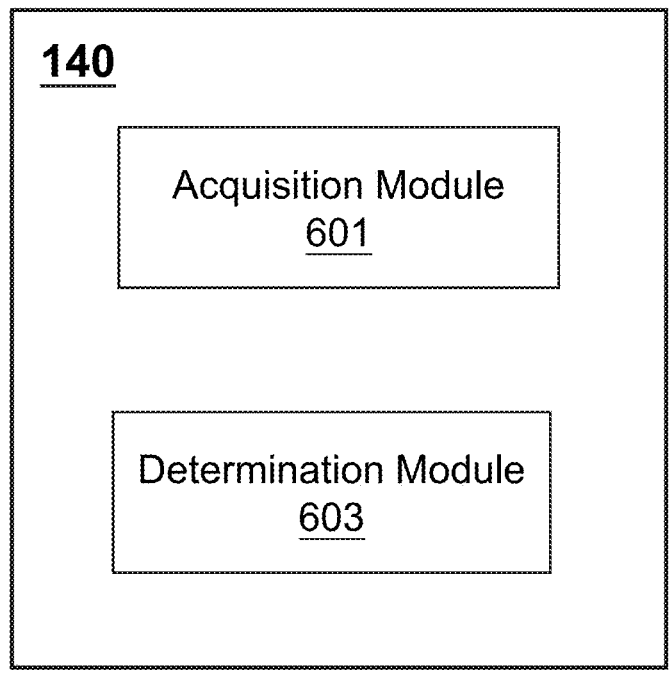
FIG. 6 is a block diagram illustrating an exemplary processing device according to some embodiments of the present disclosure.

FIG. 6 is a block diagram illustrating an exemplary processing device 140 according to some embodiments of the present disclosure. In some embodiments, a radiation delivery device (e.g., the radiation delivery device 110) may be used to perform the radiotherapy treatment. The radiation delivery device may include a first device (e.g., the treatment device 116), a second device (e.g., the imaging device 113), and a couch (e.g., the couch 114) including a mark (e.g., the mark 170) that extends along a certain direction. As shown in FIG. 6, the processing device 140 may include an acquisition module 601 and a determination module 603.

In some embodiments, the acquisition module 601 may be configured to obtain one or more first images of a couch at one or more first locations in a first device (e.g., the imaging device or the treatment device). Each of the one or more first images may be a 2D image. Each of the one or more first images may correspond to one of the one or more first locations in the first device. The couch may include a mark. A first reference plane of the first device may intersect with the mark at a plurality of first points of the mark. Each first image may include a representation of each of the plurality of first points. In some embodiments, the acquisition module 601 may further be configured to obtain correlation information between the first position and an actual position of each of the plurality of first points. In some embodiments, the acquisition module 601 may further be configured to obtain a second image of the couch at a second location in a second device (e.g., the imaging device or the treatment device). The first device may be different from the second device. A second reference plane of the second device may have a plurality of second points of the mark. In some embodiments, the acquisition module 601 may further be configured to obtain a test first image of the couch at a test location in the first device. The test first image may be a 2D image. The test first image may include a representation of a plurality of test first points of the mark. In some embodiments, the acquisition module 601 may further be configured to obtain a third image of the couch. The third image may be a 3D image.

In some embodiments, the determination module 603 may be configured to determine one or more calibration images based on the correlation information and the one or more first images. Each of the one or more calibration images may be a 2D image. In some embodiments, the determination module 603 may further be configured to determine, based on the second image, a second isocenter position of a representation of a second isocenter of the second device and a second position of a representation of each of the plurality of second points in the second image. The determination module 603 may further be configured to determine, based on the one or more calibration images, the second isocenter position, and the second positions, a difference between a location of the couch in the first device and a location of the couch in the second device.

In some embodiments, the determination module 603 may further configured to determine, from the one or more calibration images and based on the plurality of second points in the second image, a reference calibration image corresponding to the second image. The reference calibration image may be obtained at a reference first location in the first device. The determination module 603 may designate a coordinate of the reference first location along a longitudinal direction of the couch as a first coordinate of the second location along the longitudinal direction of the couch.

In some embodiments, the determination module 603 may further be configured to determine, in the reference calibration image, a reference calibration isocenter position of a representation of a first isocenter of the first device and a reference calibration position of each of the plurality of reference calibration points. In some embodiments, the determination module 603 may further be configured to determine, based on the second isocenter, the second positions, the reference calibration positions, and the reference calibration isocenter position, a difference between a location of the couch in the first device and a location of the couch in the second device along the lateral direction of the couch.

In some embodiments, the determination module 603 may be configured to determine a calibration feature among a plurality of calibration points of each of the one or more calibration images. The determination module 603 may determine a second feature among the plurality of second points of the second image. The determination module 603 may determine, based on the calibration feature and the second feature, the reference calibration image. In some embodiments, the determination module 603 may further be configured to identify, from the one or more calibration images, a calibration image having the calibration feature that matches the second feature. As used herein, that a calibration feature matches a second feature indicates that the calibration feature (or its value referred to as the calibration feature value) is deemed identical to (e.g., being similar to or the same as) the second feature (or its value referred to as the second feature value). The determination module 603 may designate the identified calibration image as the reference calibration image.

It should be noted that the above descriptions of the processing device 140 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the processing device 140 may include one or more other modules and/or one or more modules described above may be omitted. Additionally or alternatively, two or more modules may be integrated into a single module and/or a module may be divided into two or more units. However, those variations and modifications also fall within the scope of the present disclosure.

FIG. 7 is a flowchart illustrating an exemplary process for determining calibration images according to some embodiments of the present disclosure. In some embodiments, process 700 may be executed by the couch position calibration system 100. For example, the process 700 may be implemented as a set of instructions (e.g., an application) stored in a storage device (e.g., the storage device 150, the storage 220, and/or the storage 390). The processing device 140 (e.g., the processor 210 of the computing device 200, the CPU 340 of the mobile device 300, and/or one or more modules illustrated in FIG. 6) may execute the set of instructions and may accordingly be directed to perform the process 700. The operations of the illustrated process presented below are intended to be illustrative. In some embodiments, the process 700 may be accomplished with one or more additional operations not described, and/or without one or more of the operations discussed. Additionally, the order of the operations of the process 700 illustrated in FIG. 7 and described below is not intended to be limiting.

In 710, the processing device 140 (e.g., the acquisition module 601) may obtain one or more first images of a couch at one or more first locations in a first device. Each of the one or more first images may be acquired at (or referred to as corresponding to) one of the one or more first locations. The couch may include a mark (e.g., the mark 170). The mark may intersect a first reference plane of the first device at a plurality of first points.

In some embodiments, the one or more first images may be acquired by scanning the couch (e.g., the couch 114) at the one or more first locations along a longitudinal direction of the couch by the first device. In some embodiments, the first device may be an imaging device (e.g., the imaging device 113), or a treatment device (e.g., the treatment device 116). In some embodiments, the imaging device may include a CT device, for example, a cone beam computed tomography (CBCT) device, a fan-beam computed tomography (FBCT) device, a multi-slice computed tomography (MSCT), etc. In some embodiments, the treatment device may include a radiotherapy device, a linear accelerator, etc.

Each first image may be acquired when the couch is vertically (along the Z-axis direction as illustrated in FIG. 4A) irradiated by a radiation source (e.g., a CT tube) of the first device. In some embodiments, a subject (e.g., a patient) may lie on the couch at a direction along the Y-axis as illustrated in FIG. 4A. The subject may be moved back and forth between the first device (e.g., the imaging device 113) and a second device (e.g., the treatment device 116) by moving the couch. In some embodiments, a moving direction of the couch may parallel with (or substantially parallel with) the Y-axis. In some embodiments, the first location(s) may include locations arranged at regular intervals along the longitudinal direction of the couch. For example, the intervals of each two adjacent first locations along the longitudinal direction of the couch may be 0.5 centimeters, 1 centimeter, 2 centimeters, 5 centimeters, 10 centimeters, etc. In some embodiments, intervals between at least two pairs of neighboring first locations of the one or more first locations may be different. In some embodiments, intervals between at least two pairs of neighboring first locations of the one or more first locations may be identical. For instance, intervals between all pairs of neighboring first locations are identical so that all the first locations are equally spaced. As used herein, a pair of neighboring first locations refer to first locations that are next to each other without any intervening first locations in between.

The mark may intersect with the first reference plane of the first device at a plurality of first points of the mark. The first reference plane of the first device may be perpendicular to the Y-axis direction (i.e., the longitudinal direction of the couch). In some embodiments, the first device may include a radiation source, the first reference plane may be a rotating plane of the first device which refers to a plane where the radiation source of the first device rotates.

In 720, the processing device 140 (e.g., the determination module 603) may determine, in each of the one or more first images, a first position of a representation of each of the plurality of first points.

The first position of a representation of each first point of the mark refers to a projection position of the first point in the first image. The projection position of the first point in the first image may refer to the position of the projection of the first point in a detector (e.g., the detector 112). The plurality of first points may be intersection points of the first reference plane of the first device and the mark on the couch. In some embodiments, for each first image, the processing device 140 may determine the first position of each of the plurality of first points based on the first reference plane. For example, the processing device 140 may determine the first position of each of the plurality of first points according to an intersection line between the first reference plane and the couch.

In 730, the processing device 140 (e.g., the acquisition module 601) may obtain correlation information between the first position and an actual position of each of the plurality of first points. In some embodiments, the correlation information may include a magnification factor between the couch in space and the projection of the couch in each first image. More descriptions about the determining correlation information may be found elsewhere in the present disclosure (e.g., FIG. 8 and the descriptions thereof).

In 740, the processing device 140 (e.g., the acquisition module 601) may determine one or more calibration images based on the correlation information and the one or more first images.

In some embodiments, each of the one or more calibration images may include a representation of a first isocenter of the first device at a calibration isocenter position and a representation of each of a plurality of calibration points at a calibration position. Each of the plurality of calibration points may correspond to one of the plurality of first points. Specifically, the first isocenter of the first device may be a rotation center of a radiation source (e.g., the imaging radiation source 115) of the first device (e.g., the imaging device 113), or a point in space where radiation beams intersect when the radiation source is rotated during beam-on. In some embodiments, a distance between two calibration points in each calibration image may be a quotient of a distance between two first points and the correlation information, wherein the two first points are corresponding to the two calibration points.

It should be noted that the above description regarding the process 700 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

FIG. 8 is a flowchart illustrating an exemplary process for determining correlation information between a first position of each of a plurality of first points of a mark in a first image and an actual position of each of a plurality of first points of a mark according to some embodiments of the present disclosure. In some embodiments, process 800 may be executed by the couch position calibration system 100. For example, the process 800 may be implemented as a set of instructions (e.g., an application) stored in a storage device (e.g., the storage device 150, the storage 220, and/or the storage 390). The processing device 140 (e.g., the processor 210 of the computing device 200, the CPU 340 of the mobile device 300, and/or one or more modules illustrated in FIG. 6) may execute the set of instructions and may accordingly be directed to perform the process 800. The operations of the illustrated process presented below are intended to be illustrative. In some embodiments, the process 800 may be accomplished with one or more additional operations not described, and/or without one or more of the operations discussed. Additionally, the order of the operations of the process 800 illustrated in FIG. 8 and described below is not intended to be limiting.

In 810, the processing device 140 (e.g., the acquisition module 601) may obtain a test first image of a couch at a test location in a first device. The test first image may be a 2D image. The test first image may include a representation of a plurality of test first points of the mark. The plurality of test first points of the mark may be intersection points of the mark (e.g., an N-typed mark) and a first reference plane of the first device. As used herein, the test location refers to a certain location of the couch along a longitudinal direction of the couch. In some embodiments, the test location may be any location along the longitudinal direction of the couch. In some embodiments, the processing device 140 may designate a first image from the one or more first images described in FIG. 7 as the test first image. The location where the first image (that is designated as the test first image) is acquired is considered the test location. In some embodiments, the test first image may be acquired additionally at a test location, which is different from any one first image of the one or more first images.

In 820, the processing device 140 (e.g., the determination module 603) may determine, in the test first image, a test first position of a representation of each of the plurality of test first points. Similar to the first points as described in FIG. 7, the test first position of each test first point may refer to a projection position of the test first point in the test first image. More descriptions about the first positions may be found elsewhere in the present disclosure, for example, operation 720 in FIG. 7 and the descriptions thereof, which are not repeated here.

In 830, the processing device 140 (e.g., the acquisition module 601) may obtain a third image (e.g., a three-dimensional (3D) image) of the couch at the test location.

The third image may be acquired when the couch is located at the test location. For example, when the couch (e.g., the couch 114) is located at the test location, the first device (e.g., the imaging device 113 or the treatment device 116) may acquire images of the couch at different irradiation angles. The processing device 140 may generate the third image of the couch based on the images acquired from different irradiation angles. The third image may include a plurality of intersection points of the mark (e.g., an N-typed mark) and the first reference plane of the first device (i.e., the plurality of test first points of the mark) at the test location, e.g., points a, b, and c. The processing device 140 may determine an actual position (i.e., a spatial location) of the plurality of intersection points based on the third image.

In 840, the processing device 140 (e.g., the determination module 603) may determine, based on the test first image and the third image, correlation information between the test first positions of the plurality of test first points in the test first image and actual positions of the plurality of test first points in the couch. In some embodiments, the correlation information may include a magnification factor between the couch (e.g., the mark in the couch) in space and the projection of the couch (e.g., the projection of the mark) in the test first image. For example, if an actual distance between points a and b in the third image is ab, and a projection distance of the points a and b in the test first image is ab*, the correlation information may be expressed as ab*/ab.

It should be noted that the above description regarding the process 800 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 9:
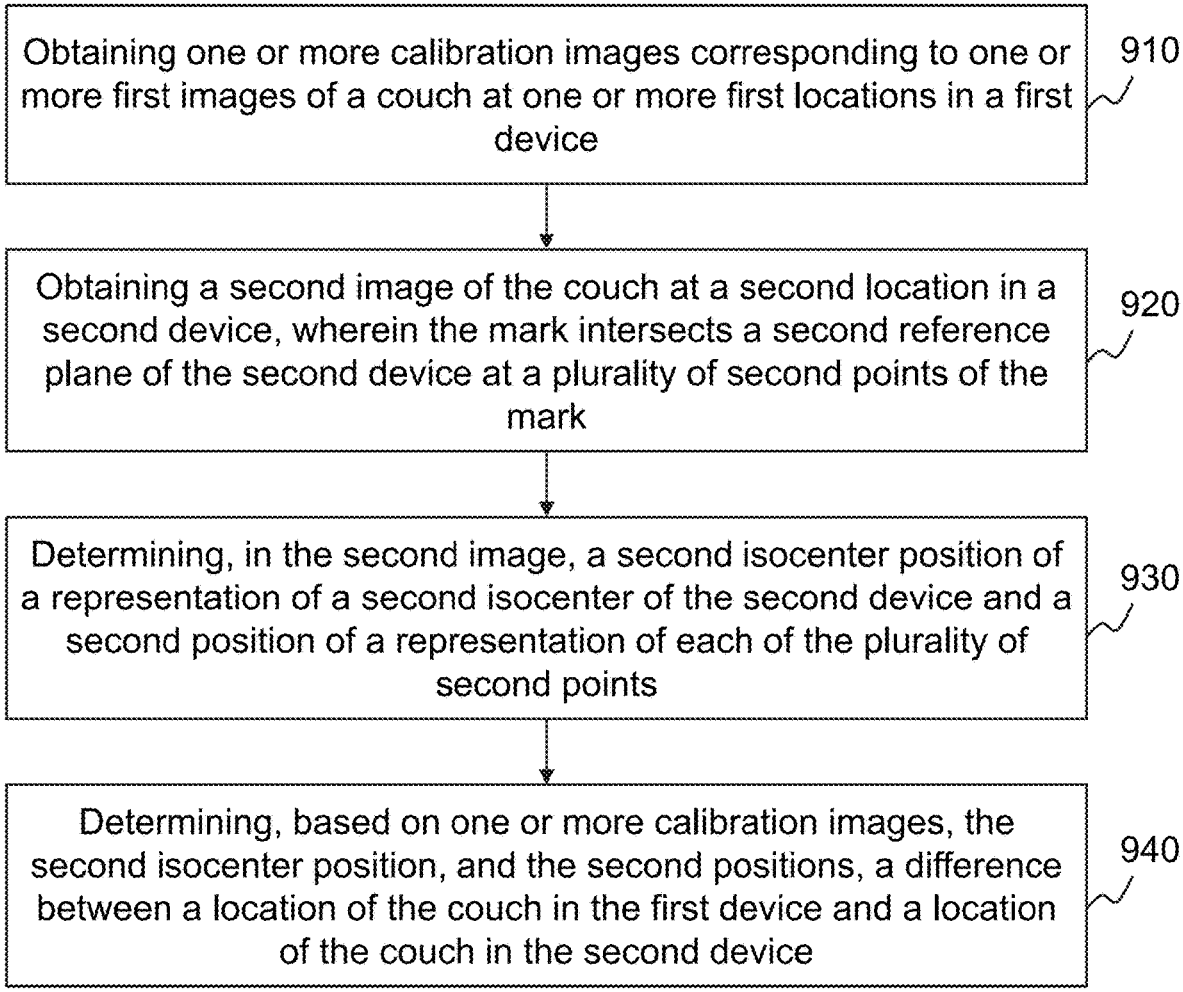
FIG. 9 is a flowchart illustrating an exemplary process for calibrating a couch position according to some embodiments of the present disclosure.

FIG. 9 is a flowchart illustrating an exemplary process for calibrating a couch position according to some embodiments of the present disclosure. In some embodiments, process 900 may be executed by the couch position calibration system 100. For example, the process 900 may be implemented as a set of instructions (e.g., an application) stored in a storage device (e.g., the storage device 150, the storage 220, and/or the storage 390). The processing device 140 (e.g., the processor 210 of the computing device 200, the CPU 340 of the mobile device 300, and/or one or more modules illustrated in FIG. 6) may execute the set of instructions and may accordingly be directed to perform the process 900. The operations of the illustrated process presented below are intended to be illustrative. In some embodiments, the process 900 may be accomplished with one or more additional operations not described, and/or without one or more of the operations discussed. Additionally, the order of the operations of the process 900 illustrated in FIG. 9 and described below is not intended to be limiting.

In 910, the processing device 140 (e.g., the determination module 603) may obtain one or more calibration images corresponding to one or more first images of a couch at one or more first locations in a first device.

Each of the one or more first images may be acquired at one of the one or more first locations. The couch may include a mark (e.g., the mark 170). A first reference plane of the first device may have a plurality of first points of the mark.

Each calibration image may include correlation information between a first position of a representation of each of the plurality of first points and an actual position of the each of the plurality of first points. In some embodiments, the correlation information may include a magnification factor between the couch in space and the projection of the couch in the calibration image. More descriptions of the one or more first images and calibration images may be found elsewhere in the present disclosure. See, e.g., FIG. 7 and the descriptions thereof.

In 920, the processing device 140 (e.g., the acquisition module 601) may obtain a second image of the couch at a second location in a second device. In some embodiments, the second image may be a 3D image. A second reference plane of the second device may intersect the mark at a plurality of second points of the mark.

Before performing operation 920, the processing device 140 may cause the couch to be moved from the first device to the second device. In some embodiments, the first device may include an imaging device (e.g., a CT device), and the second device may include a treatment device (e.g., a radiotherapy device). In some embodiments, the first device may include a treatment device, and the second device may include a imaging device. The couch may be moved between the imaging device and the treatment device.

As used herein, the second location refers to a location where the couch is irradiated by a radiation source of the second device (e.g., the treatment radiation source 117 of the treatment device). For example, when the second device is a treatment device, a patient (e.g., the patient 503) may lie on the couch for treatment. The radiation source of the treatment device may irradiate a lesion area (e.g., the lesion area 502) of the patient to achieve the purpose of treatment. When the lesion area of the patient is irradiated by the radiation source of the treatment device, the corresponding location of the couch may be the second location. In some embodiments, the second location may be set according to a default setting of the second device (or the couch position calibration system 100) or preset by a user or operator.

In some embodiments, the second image may be acquired when the couch is vertically irradiated by the radiation source of the second device. In some embodiments, the second image may be acquired by an additional radiation source installed on the second device. As used herein, the second reference plane may be a rotating plane of the second device which refers to a plane where the radiation source of the second device rotates. The second reference plane of the second device may be perpendicular to the Y-axis direction (i.e., the longitudinal direction of the couch). In some embodiments, the second device may be an MRI device. As used herein, the second reference plane of the second device may be a plane being perpendicular to the Y-axis direction and including an iso-center of the MRI device.

In 930, the processing device 140 (e.g., the determination module 603) may determine, in the second image, a second isocenter position of a second isocenter of the second device and a second position of a representation of each of the plurality of second points.

As used herein, the second isocenter (e.g., denoted as O) of the second device refers to a mechanical center of the second device. Specifically, the second isocenter O of the second device may be a rotation center of the radiation source (e.g., the treatment radiation source 117) of the second device (e.g., the treatment device 116), or a point in space where radiation beams intersect when the radiation source is rotated during beam-on. The second isocenter position refers to a projection position of the second isocenter O of the second device in the second image. In some embodiments, the second isocenter position may be located at the center of the second image. In some embodiments, a second Cartesian coordinate system may be established based on a certain point in the second image as an origin. The second isocenter position may refer to coordinates of the second isocenter O in the second rectangular coordinate system. In some embodiments, the processing device 140 may determine the second isocenter position corresponding to the second image by, for example, a Huffman transformation based computer program. The processing device 140 may determine a center of a radiation field of view of the second image, thereby determining the second isocenter position. In some embodiments, the processing device 140 may determine the second isocenter position corresponding to the second image based on historical data that has been acquired and stored in a storage device (e.g., the storage device 150). For example, a plurality of historical second images may be stored in the storage device. Before storing each of the plurality of historical second images in the storage device, the processing device 140 may determine the corresponding historical second isocenter position (e.g., the center of radiation field of view). The processing device 140 may match the second image with the historical second image. The processing device 140 may determine the historical second isocenter position of the historical second image that matches the second image as the second isocenter position of the second image. As used herein, that the second image matches with the historical second image refers to that when the two images are acquired, the locations of the couch and angles of the gantry are the same.

As used herein, the second position of a representation of a second point of the mark refers to a projection position of the second point in the second image. The projection position of the second point in the second image may refer to the position of the projection of the second point in a detector (e.g., a detector in the treatment device 116). In some embodiments, the plurality of second points may be intersection points of the second reference plane of the second device and the mark on the couch. The second isocenter O of the second device may be a rotation center of the second device 116 on the second reference plane. That is to say, both the plurality of second points and the second isocenter O of the second device may be on the second reference plane. In some embodiments, for each second image, the processing device 140 may determine the second isocenter position of the second isocenter O of the second device and the second position of each of the plurality of second points based on the second reference plane. For example, the processing device 140 may determine the second position of each of the plurality of second points according to an intersection line between the second reference plane and the couch. In some embodiments, in the second image, the second isocenter position of the second isocenter O of the second device and the second position of each of the plurality of second points may be on a same line.

In 940, the processing device 140 (e.g., the determination module 603) may determine, based on the one or more calibration images, the second isocenter position, and the second positions, a difference between a location of the couch in the first device and a location of the couch in the second device.

As used herein, the difference between a location of the couch in the first device and a location of the couch in the second device refers to a relationship between the location of the couch in the first device and the location of the couch in the second device. In some embodiments, the difference between a location of the couch in the first device and a location of the couch in the second device may include at least one of a location difference in the X-axis direction (i.e., the lateral direction of the couch), a location difference in the Y-axis direction (i.e., the longitudinal direction of the couch), or a location difference in the Z-axis direction (i.e., the vertical direction of the couch). In some embodiments, the difference between the location of the couch in the first device and the location of the couch in the second device may include a difference of the first coordinate of the second location along the longitudinal direction of the couch, and a difference between the location of the couch in the first device and the location of the couch in the second device along the lateral direction of the couch.

In some embodiments, the processing device 140 may determine, from the one or more calibration images and based on the plurality of second points in the second image, a reference calibration image corresponding to the second image. As used herein, a calibration image (e.g., a reference calibration image) is considered corresponding to a second image if at least one specific feature (or its value referred to as the calibration feature value) of the calibration image is deemed identical to a corresponding feature (or its value referred to as the second feature value) of the second image. In some embodiments, a feature value of an image (e.g., a calibration image, a second image) may be assessed based on a representation of the mark, or a portion thereof (e.g., one or more points of the mark) in the image. The reference calibration image may be obtained at a reference first location. The processing device 140 may further designate a coordinate of the reference first location along a direction (e.g., the longitudinal direction) of the couch (i.e., the Y-axis) as a first coordinate of the second location along a corresponding direction (e.g., the longitudinal direction of the couch). More descriptions for determining the reference calibration image may be found elsewhere in the present disclosure (e.g., FIG. 10 and the descriptions thereof).

In some embodiments, the processing device 140 may determine, in the reference calibration image, a reference calibration isocenter position of a representation of the first isocenter of the first device and a reference calibration position of each of the plurality of reference calibration points. The processing device 140 may further determine, based on the second isocenter, the second positions, the reference calibration positions, and the reference calibration isocenter position, a difference between a location of the couch in the first device and a location of the couch in the second device along the lateral direction of the couch (i.e., the X-axis). More descriptions in this regard may be found elsewhere in the present disclosure (e.g., FIG. 11 and the descriptions thereof).

In some embodiments, the difference between a location of the couch in the first device and a location of the couch in the second device along the lateral direction of the couch may include an (actual) offset of the couch at locations in the X-axis direction in the first device and the second device, respectively, in the physical world.

It should be noted that the above description regarding the process 900 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 10:
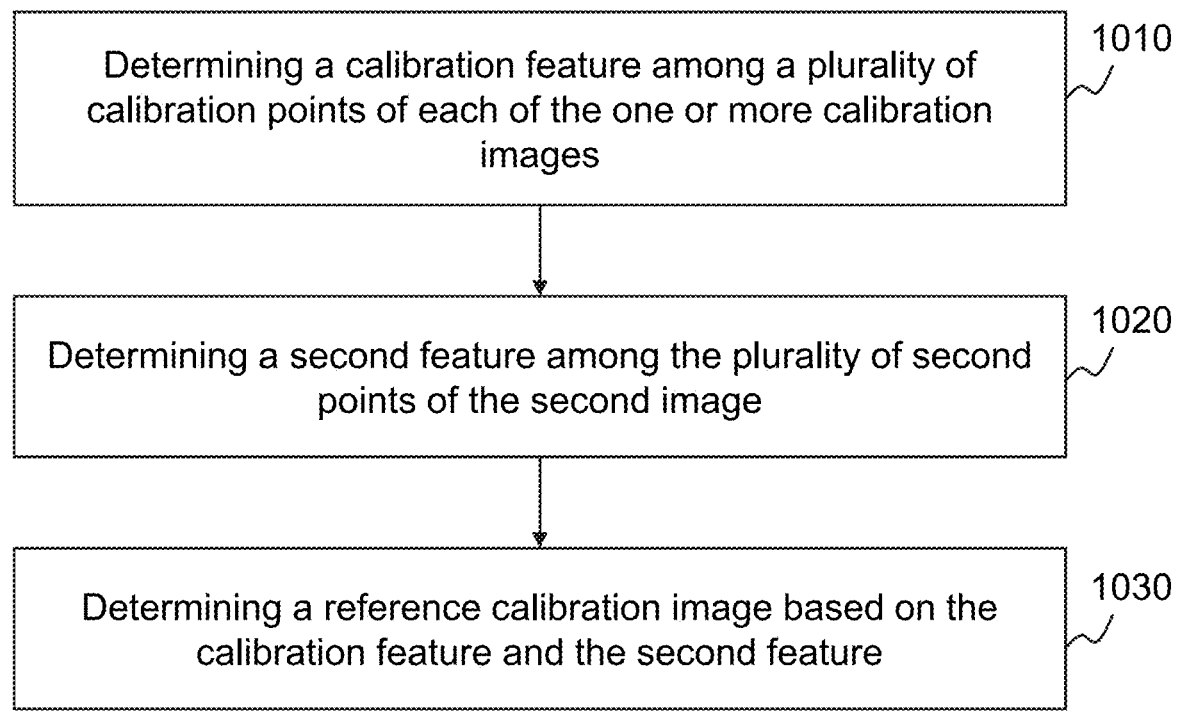
FIG. 10 is a flowchart illustrating an exemplary process for determining a reference calibration image according to some embodiments of the present disclosure.

FIG. 10 is a flowchart illustrating an exemplary process for determining a reference calibration image according to some embodiments of the present disclosure. In some embodiments, process 1000 may be executed by the couch position calibration system 100. For example, the process 1000 may be implemented as a set of instructions (e.g., an application) stored in a storage device (e.g., the storage device 150, the storage 220, and/or the storage 390). The processing device 140 (e.g., the processor 210 of the computing device 200, the CPU 340 of the mobile device 300, and/or one or more modules illustrated in FIG. 6) may execute the set of instructions and may accordingly be directed to perform the process 1000. The operations of the illustrated process presented below are intended to be illustrative. In some embodiments, the process 1000 may be accomplished with one or more additional operations not described, and/or without one or more of the operations discussed. Additionally, the order of the operations of the process 1000 illustrated in FIG. 10 and described below is not intended to be limiting.

In 1010, the processing device 140 (e.g., the determination module 603) may determine a calibration feature among a plurality of calibration points of each of the one or more calibration images. Each of the plurality of calibration points may correspond to one of the plurality of first points.

As used herein, the calibration feature refers to a calibration feature value of the plurality of calibration points in the calibration image. For illustration purposes, assuming that the plurality of calibration points in the calibration image may include three points A*, B*, and C*. Point B* is located between point A* and point C* in the calibration image. Calibration positions of the one or more calibration points may be positions of (the representation of) the one or more calibration points (e.g., points A*, B*, and C*) in the calibration image. In some embodiments, the calibration feature may refer to a calibration relationship among the one or more calibration points, such as, a spatial relationship between points A* and B*, a spatial relationship between points B* and C*, etc. In some embodiments, the calibration relationship among the one or more calibration points may be represented by the calibration feature value. In some embodiments, the calibration feature may include a third distance between points A* and B* (e.g., denoted as A*B*) determined based on their respective calibration positions in a calibration image, a fourth distance between points B* and C* (e.g., denoted as B*C*) determined based on their respective calibration positions in the calibration image, a ratio of the third distance to the fourth distance (e.g., denoted as A*B*/B*C*), a ratio of the fourth distance to the third distance (e.g., denoted as B*C*/A*B*), a difference between the third distance and the fourth distance, or the like, or any combination thereof.

In 1020, the processing device 140 (e.g., the determination module 603) may determine a second feature among the plurality of second points of the second image. For the purpose of illustration, assuming that the plurality of second points of the second image may include three points A, B, and C. Point B is located between point A and point C in the second image. Second positions of the one or more second points may be positions of (the representation of) the one or more second points (e.g., points A, B, and C) in a second image. In some embodiments, the second feature may refer to a second relationship among the one or more second points, such as, a spatial relationship between points A and B, a spatial relationship between points B and C, etc. In some embodiments, the second relationship among the one or more second points may be represented by a second feature value. In some embodiments, the second feature may include a first distance between points A and B (e.g., denoted as AB) determined based on their respective second positions in the second image, a second distance between points B and C (e.g., denoted as BC) determined based on their respective second positions in the second image, a ratio of the first distance to the second distance (e.g., denoted as AB/BC), a ratio of the second distance to the first distance (e.g., denoted as BC/AB), a difference between the first distance and the second distance, or the like, or any combination thereof.

Figure 5D:
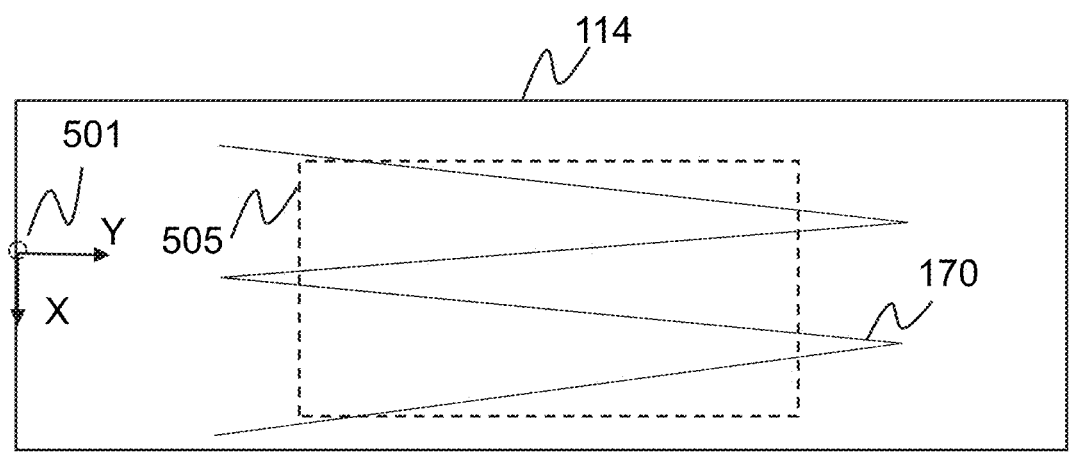
FIG. 5D is a schematic diagram of an exemplary couch according to some embodiments of the present disclosure.

It should be noted that, when a distance between points A and C is a fixed distance, the distance AC between points A and C cannot be used to determine the second feature. For example, when the mark is an N-shaped mark (e.g., the mark 170 as illustrated in FIG. 5A), since the two side lines of the N-shaped mark 170 are parallel, the distance between the two side lines is fixed regardless of the location of the couch 114 along the longitudinal direction of the couch 114, i.e., a distance between points A and C is fixed and should not be used to determine the second feature. As another example, when the mark is a W-shaped mark (as shown in FIG. 5D), the distance between the two outermost side lines changes as the location of the couch 114 changes along the longitudinal direction of the couch 114, i.e., the distance between points A and C varies and can be used to determine the second feature.

In 1030, the processing device 140 (e.g., the determination module 603) may determine a reference calibration image based on the calibration feature and the second feature. In some embodiments, the processing device 140 may identify, from the one or more calibration images, a calibration image having the calibration feature that matches the second feature. The processing device 140 may designate the identified calibration image as the reference calibration image.

As used herein, that the calibration feature matches the second feature refers to that the calibration feature (or its value referred to as the calibration feature value) is deemed identical to (e.g., being similar to or the same as) the second feature (or its value referred to as the second feature value). In some embodiments, the processing device 140 may identify a calibration image having a calibration feature identical to the second feature from the one or more calibration images. For example, if the ratio AB/BC of the first distance to the second distance of the plurality of second points in the second image is 0.4, the processing device 140 may identify a calibration image whose ratio A*B*/B*C* of the third distance to the fourth distance of the plurality of calibration points is 0.4 from the one or more calibration images. As another example, if the first distance AB between points A and B in the second image is 15 centimeters, the processing device 140 may identify a calibration image with a third distance A*B* of 15 centimeters between points A* and B* of the plurality of calibration points from the one or more calibration images.

In some embodiments, when among the one or more calibration images there is no calibration image having the calibration feature identical to the second feature, the processing device 140 may identify, among the one or more calibration images, a calibration image having the calibration feature closest or most similar to the second feature. For example, if the ratio AB/BC of the first distance to the second distance of the plurality of second points in the second image is 0.4, and the one or more calibration images do not have a calibration image whose ratio A*B*/B*C* of the third distance to the fourth distance of the plurality of calibration points is 0.4, the processing device 140 may identify a calibration image whose ratio of the third distance to the fourth distance of the plurality of calibration points closest or most similar to 0.4 (e.g., 0.38) from the one or more calibration images. As another example, if the first distance AB between points A and B in the second image is 15 centimeters, and the one or more calibration images do not have a calibration image whose third distance A*B* between points A* and B* of the plurality of calibration points is 15 centimeters, the processing device 140 may identify a calibration image with a third distance A*B* closest or most similar to 15 (e.g., 15.2 centimeters) centimeters between points A* and B* of the plurality of calibration points from the one or more calibration images.

It should be noted that the above description regarding the process 1000 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

FIG. 11 is a flowchart illustrating an exemplary process for determining a difference between a location of the couch in the first device and a location of the couch in the second device according to some embodiments of the present disclosure. In some embodiments, process 1100 may be executed by the couch position calibration system 100. For example, the process 1100 may be implemented as a set of instructions (e.g., an application) stored in a storage device (e.g., the storage device 150, the storage 220, and/or the storage 390). The processing device 140 (e.g., the processor 210 of the computing device 200, the CPU 340 of the mobile device 300, and/or one or more modules illustrated in FIG. 6) may execute the set of instructions and may accordingly be directed to perform the process 1100. The operations of the illustrated process presented below are intended to be illustrative. In some embodiments, the process 1100 may be accomplished with one or more additional operations not described, and/or without one or more of the operations discussed. Additionally, the order of the operations of the process 1100 illustrated in FIG. 11 and described below is not intended to be limiting.

In 1110, the processing device 140 (e.g., the determination module 603) may determine a reference calibration image corresponding to a second image from one or more calibration images based on a plurality of second points in the second image. The reference calibration image may be determined based on a reference first image. The reference first image may be obtained at a reference first location in the first device. In some embodiments, the reference calibration image may be determined based on the correlation information and the reference first image.

In 1120, the processing device 140 (e.g., the determination module 603) may designate a coordinate of the reference first location along the longitudinal direction of the couch as a first coordinate of a second location along the longitudinal direction of the couch.

In some embodiments, since the reference calibration image matches the second image, a location of the couch along the Y-axis direction in the second device when the second image is acquired in the second device may correspond to a location of the couch along the Y-axis direction in the first device when the first image corresponding to the reference calibration image is acquired in the first device. The processing device 140 may designate a coordinate of the couch in the longitudinal direction when the reference first image is acquired (i.e., a Y-axis coordinate of the reference first location) as the first coordinate of the second location along the longitudinal direction (i.e., a Y-axis coordinate of the second location). For example, taking a midpoint on a side of the couch (e.g., the leftmost edge or side of the couch 114 as illustrated in FIG. 4A) as an origin of a coordinate system in the imaging device (e.g., the coordinate system 404), the coordinate of the couch in the Y-axis direction may be 50 centimeters, which indicates that the reference first location of the couch is 50 centimeters away from the origin in the Y-axis direction. Therefore, in the same coordinate system, the Y-axis coordinate (i.e., the first coordinate) of the second location corresponding to the second image may also be 50 centimeters.

In 1130, the processing device 140 (e.g., the determination module 603) may determine, in the reference calibration image, a reference calibration isocenter position of a representation of a first isocenter of the first device and a reference calibration position of each of a plurality of reference calibration points in the reference calibration image.

In some embodiments, the processing device 140 may determine the reference calibration isocenter position in a manner similar to how the second isocenter position is determined as described in operation 930. In some alternative embodiments, after a calibration isocenter position corresponding to each of one or more calibration images is determined, the processing device 140 may store the calibration isocenter position corresponding to each the one or more calibration images into a storage device (e.g., the storage device 150). After the reference calibration image matching the second image is determined, the processing device 140 may directly retrieve the reference calibration isocenter position corresponding to the reference calibration image from the storage device.

In some embodiments, the processing device 140 may determine the reference calibration position in a manner similar to how the second position is determined as described in operation 930. In some alternative embodiments, after determining the calibration positions of the plurality of calibration points corresponding to each of the one or more calibration image, the processing device 140 may store the calibration positions corresponding to each the one or more calibration image into a storage device (e.g., the storage device 150). After the reference calibration image matching the second image is determined, the processing device 140 may directly retrieve the reference calibration positions corresponding to the reference calibration image from the storage device.

In 1140, the processing device 140 (e.g., the determination module 603) may determine, based on the second isocenter position (e.g., the second isocenter position determined in 930), the second positions, the reference calibration positions, and the reference calibration isocenter position, a difference between a location of the couch in the first device and a location of the couch in the second device along the lateral direction of the couch.

After the reference calibration isocenter position and the reference calibration positions of the plurality of reference calibration points in the reference calibration image are determined, the processing device 140 may determine the difference between the location of the couch in the first device and the location of the couch in the second device both along the lateral direction of the couch. In some embodiments, the difference between the location of the couch in the first device and the location of the couch in the second device both along the lateral direction of the couch may include a relative relationship between the reference calibration isocenter position in the reference calibration image and a second isocenter position in the second image. For example, the processing device 140 may determine a distance L between the reference calibration isocenter position and any one of the reference calibration positions (such as point B*) based on the reference calibration image. The processing device 140 may determine a distance I between the second isocenter position and a corresponding second position (such as point B, which corresponding to B*) based on the second image. The difference between the two distances (i.e., the distance L and distance I) may be regarded as the difference between the location of the couch in the first device and the location of the couch in the second device, that is, an offset of the couch at locations in the X-axis direction in the first device and the second device.

It should be noted that the above description regarding the process 1100 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for couch position calibration implemented on a machine including at least one processor and at least one storage device, the method comprising:
obtaining one or more first images of a couch at one or more first locations in a first device, each of the one or more first images corresponding to one of the one or more first locations, the first device including an imaging device or a treatment device, wherein the couch includes a mark, and the mark intersects a first reference plane of the first device at a plurality of first points of the mark, the first reference plane being perpendicular to a longitudinal direction of the couch or the first reference plane being a rotating plane of the first device, the couch being configured to move between the first device and a second device along the longitudinal direction;

determining, in each of the one or more first images, a first position of a representation of each of the plurality of first points, the first position of the representation of each of the plurality of first points in each of the one or more first images referring to a position of the first point in the each of the one or more first images;

obtaining correlation information between respective positions of the plurality of first points in different coordinate systems, the correlation information including a magnification factor between a position of the couch in space and a position of the couch in the each of the one or more first images;

obtaining a second image of the couch at a second location in the second device; and performing a couch position calibration by determining, based on the second image, the correlation information, and the one or more first images, a difference between a location of the couch in the first device and a location of the couch in the second device along a lateral direction of the couch.

2. The method of claim 1, wherein the one or more first locations include locations arranged at regular intervals along the longitudinal direction of the couch.

3. The method of claim 1, wherein the mark includes at least one of an N-shaped mark, an M-shaped mark, an S-shaped mark, a V-shaped mark, an A-shaped mark, or a W-shaped mark.

4. The method of claim 1, wherein the obtaining correlation information between respective positions of the plurality of first points in different coordinate systems comprises:
   obtaining a test first image of the couch at a test location in the first device, the test first image including a representation of a plurality of test first points of the mark;
   determining, in the test first image, a test first position of a representation of each of the plurality of test first points, the test first position of a representation of each of the plurality of test first points referring to a position of the test first point in the test first image;
   obtaining images of the couch acquired by the first device at different irradiation angles;
   generating a third image of the couch based on the images acquired from different irradiation angles, the third image being a three-dimensional (3D) image;
   determining spatial locations of the plurality of test first points in the couch based on the third image;
   determining, based on the test first positions of the plurality of test first points and the spatial locations of the plurality of test first points in the couch, the correlation information.

5. The method of claim 4, wherein at least one of the one or more first images or the test first image is a 2D image, the first position of the representation of each of the plurality of first points in each of the one or more first images referring to a projection position of the first point in the each of the one or more first images, and the test first position of a representation of each of the plurality of test first points referring to a projection position of the test first point in the test first image.

6. The method of claim 1, wherein
the one or more first images are acquired by the first device; and
performing the couch position calibration based on the correlation information and the one or more first images includes:
determining one or more calibration images based on the correlation information and the one or more first images, wherein for each of the one or more calibration images,
   the each of the one or more calibration images includes a representation of a first isocenter of the first device at a calibration isocenter position and a representation of a plurality of calibration points, each of the plurality of calibration points corresponding to one of the plurality of first points,
   the calibration isocenter position is located at a center of the each of the one or more calibration images; and
   a distance between two calibration points in the each of the one or more calibration images is determined based on a distance between two corresponding first points in one of the one or more first images and the correlation information; and
performing the couch position calibration based on the one or more calibration images.

7. The method of claim 6, wherein:
the mark intersects a second reference plane of the second device at a plurality of second points of the mark; and
the performing a couch position calibration by determining, based on the second image, the correlation information, and the one or more first images, a difference between a location of the couch in the first device and a location of the couch in the second device along a lateral direction of the couch includes:
   determining, in the second image, a second isocenter position of a representation of a second isocenter of the second device and a second position of a representation of each of the plurality of second points;
   determining, from the one or more calibration images and based on the plurality of second points in the second image, a reference calibration image corresponding to the second image; and
   determining, based on the one or more calibration images, the second isocenter position, and the second positions, the difference between the location of the couch in the first device and the location of the couch in the second device, including:
      designating a coordinate of a reference first location along the longitudinal direction of the couch as a first coordinate of the second location along the longitudinal direction of the couch, the reference first location referring to one of the one or more first locations at which the first image corresponding to the reference calibration image is obtained; or
      determining the difference between the location of the couch in the first device and the location of the couch in the second device along the lateral direction of the couch based on a reference calibration isocenter position of a representation of the first isocenter of the first device in the reference calibration image and the second isocenter position in the second image.

8. The method of claim 7, wherein the determining, from the one or more calibration images and based on the plurality of second points in the second image, a reference calibration image comprises:
determining a calibration feature among the plurality of calibration points of each of the one or more calibration images, the calibration feature referring to a spatial relationship among the plurality of calibration points;
determining a second feature among the plurality of second points of the second image, the second feature referring to a spatial relationship among the plurality of second points; and
determining, based on the calibration feature and the second feature, the reference calibration image.

9. The method of claim 8, wherein the determining, based on the calibration feature and the second feature, the reference calibration image comprises:
selecting one of the one or more calibration images having the calibration feature that is closest to the second feature; and
designating the selected calibration image as the reference calibration image.

10. The method of claim 9, wherein
the plurality of second points includes a point A, a point B, and a point C, and
the second feature includes at least one of a first distance between the point A and the point B, a second distance between the point B and the point C, a ratio of the first distance to the second distance, a ratio of the second distance to the first distance, or a difference between the first distance and the second distance.

11. The method of claim 7, wherein the determining the difference between the location of the couch in the first device and the location of the couch in the second device along the lateral direction of the couch based on a reference calibration isocenter position of a representation of the first isocenter of the first device in the reference calibration image and the second isocenter position in the second image includes:
determining, in the reference calibration image, the reference calibration isocenter position of the representation of the first isocenter of the first device, and a reference calibration position of each of a plurality of reference calibration points;
determining a first distance between the reference calibration isocenter position and one of the reference calibration positions;
determining a second distance between the second isocenter position and the second position corresponding to the one of the reference calibration positions; and
determining a difference between the first distance and the second distance as the difference between the location of the couch in the first device and the location of the couch in the second device along the lateral direction of the couch.

12. The method of claim 7, wherein the differences between the location of the couch in the first device and the location of the couch in the second device both along the lateral direction of the couch includes a relative position relationship between the reference calibration isocenter position in the reference calibration image and the second isocenter position in the second image.

13. The method of claim 1, wherein
the first device includes the imaging device, and the second device includes the treatment device; or
the first device includes the treatment device, and the second device includes the imaging device.

14. The method of claim 1, wherein the mark includes a continuous line intersecting the first reference plane at the plurality of first points, and in the longitudinal direction of the couch, a length of the continuous line is equal to or greater than a length of a field of view of the first device.

15. The method of claim 1, wherein the imaging device includes a CT device, and the treatment device includes a radiotherapy device.

16. A system for couch position calibration, comprising:
at least one storage device storing executable instructions, and
at least one processor in communication with the at least one storage device, when executing the executable instructions, causing the system to perform operations including:
obtaining one or more first images of a couch at one or more first locations in a first device, each of the one or more first images corresponding to one of the one or more first locations, the first device including an imaging device or a treatment device, wherein the couch includes a mark, and the mark intersects a first reference plane of the first device at a plurality of first points of the mark, the first reference plane being perpendicular to a longitudinal direction of the couch or the first reference plane being a rotating plane of the first device, the couch being configured to move between the first device and a second device along the longitudinal direction;
determining, in each of the one or more first images, a first position of a representation of each of the plurality of first points, the first position of the representation of each of the plurality of first points in each of the one or more first images referring to a position of the first point in the each of the one or more first images;
obtaining correlation information between respective positions of the plurality of first points in different coordinate systems, the correlation information including a magnification factor between a position of the couch in space and a position of the couch in the each of the one or more first images;
obtaining a second image of the couch at a second location in the second device; and
performing a couch position calibration by determining, based on the second image, the correlation information, and the one or more first images, a difference between a location of the couch in the first device and a location of the couch in the second device along a lateral direction of the couch.

17. The system of claim 16, wherein the obtaining correlation information between respective positions of the plurality of first points in different coordinate systems comprises:
obtaining a test first image of the couch at a test location in the first device, the test first image including a representation of a plurality of test first points of the mark;
determining, in the test first image, a test first position of a representation of each of the plurality of test first points, the test first position of a representation of each of the plurality of test first points referring to a position of the test first point in the test first image;
obtaining images of the couch acquired by the first device at different irradiation angles;
generating a third image of the couch based on the images acquired from different irradiation angles, the third image being a three-dimensional (3D) image;

determining spatial locations of the plurality of test first points in the couch based on the third image;

determining, based on the test first positions of the plurality of test first points and the spatial locations of the plurality of test first points in the couch, the correlation information.

18. The system of claim 16, wherein the one or more first images are acquired by the first device;

the mark intersects a second reference plane of the second device at a plurality of second points of the mark; and performing a couch position calibration by determining, based on the second image, the correlation information, and the one or more first images, a difference between a location of the couch in the first device and a location of the couch in the second device along a lateral direction of the couch includes:

determining one or more calibration images based on the correlation information and the one or more first images, wherein for each of the one or more calibration images, the each of the one or more calibration images includes a representation of a first isocenter of the first device at a calibration isocenter position and a representation of a plurality of calibration points, each of the plurality of calibration points corresponding to one of the plurality of first points, the calibration isocenter position is located at a center of the each of the one or more calibration images; and a distance between two calibration points in the each of the one or more calibration images is determined based on a distance between two corresponding first points in one of the one or more first images and the correlation information; and determining, in the second image, a second isocenter position of a representation of a second isocenter of the second device and a second position of a representation of each of the plurality of second points;

determining, from the one or more calibration images and based on the plurality of second points in the second image, a reference calibration image corresponding to the second image; and determining, based on the one or more calibration images, the second isocenter position, and the second positions, a difference between a location of the couch in the first device and a location of the couch in the second device, including:

designating a coordinate of a reference first location along the longitudinal direction of the couch as a first coordinate of the second location along the longitudinal direction of the couch, the reference first location referring to one of the one or more first locations at which the first image corresponding to the reference calibration image is obtained; or determining the difference between the location of the couch in the first device and the location of the couch in the second device along the lateral direction of the couch based on a reference calibration isocenter position of a representation of the first isocenter of the first device in the reference calibration image and the second isocenter position in the second image.

19. The system of claim 18, wherein the determining the difference between the location of the couch in the first device and the location of the couch in the second device along the lateral direction of the couch based on a reference calibration isocenter position of a representation of the first isocenter of the first device in the reference calibration image and the second isocenter position in the second image includes:

determining, in the reference calibration image, the reference calibration isocenter position of the representation of the first isocenter of the first device, and a reference calibration position of each of a plurality of reference calibration points;

determining a first distance between the reference calibration isocenter position and one of the reference calibration positions;

determining a second distance between the second isocenter position and the second position corresponding to the one of the reference calibration positions; and determining a difference between the first distance and the second distance as the difference between the location of the couch in the first device and the location of the couch in the second device along the lateral direction of the couch.

20. A non-transitory computer readable medium, comprising at least one set of instructions for couch position calibration, wherein when executed by one or more processors of a computing device, the at least one set of instructions causes the computing device to perform a method, the method comprising:

obtaining one or more first images of a couch at one or more first locations in a first device, each of the one or more first images corresponding to one of the one or more first locations, the first device including an imaging device or a treatment device, wherein the couch includes a mark, and the mark intersects a first reference plane of the first device at a plurality of first points of the mark, the first reference plane being perpendicular to a longitudinal direction of the couch or the first reference plane being a rotating plane of the first device, the couch being configured to move between the first device and a second device along the longitudinal direction;

determining, in each of the one or more first images, a first position of a representation of each of the plurality of first points, the first position of the representation of each of the plurality of first points in each of the one or more first images referring to a position of the first point in the each of the one or more first images;

obtaining correlation information between respective positions of the plurality of first points in different coordinate systems, the correlation information including a magnification factor between a position of the couch in space and a position of the couch in the each of the one or more first images;

obtaining a second image of the couch at a second location in the second device; and performing a couch position calibration by determining, based on the second image, the correlation information, and the one or more first images, a difference between a location of the couch in the first device and a location of the couch in the second device along a lateral direction of the couch.

\* \* \* \* \*